United States Patent [19]

Mann

[11] 4,267,396
[45] May 12, 1981

[54] PRODUCTION OF SODIUM AND POTASSIUM ALKOXIDES

[75] Inventor: Seymour Mann, New York, N.Y.

[73] Assignee: Aceto Chemical Co, Inc., New York, N.Y.

[21] Appl. No.: 102,237

[22] Filed: Dec. 10, 1979

Related U.S. Application Data

[63] Continuation-in-part of Ser. No. 4,712, Jan. 19, 1979, abandoned.

[51] Int. Cl.³ .................... C07C 29/70; C07C 29/94
[52] U.S. Cl. ............................................. 568/851
[58] Field of Search ...................................... 568/851

[56] References Cited

U.S. PATENT DOCUMENTS

| | | | |
|---|---|---|---|
| 1,712,830 | 5/1926 | Kyrides | 568/851 |
| 2,278,550 | 4/1942 | Loder et al. | 568/851 |

FOREIGN PATENT DOCUMENTS

| | | | |
|---|---|---|---|
| 164297 | 8/1904 | Fed. Rep. of Germany | 568/851 |
| 148392 | 12/1962 | U.S.S.R. | 568/851 |

OTHER PUBLICATIONS

Bulgatsch et al., "Chem. Zentr.", I (1936), p. 642.

*Primary Examiner*—Joseph E. Evans
*Attorney, Agent, or Firm*—Steinberg & Raskin

[57] ABSTRACT

Sodium and potassium alkoxides are produced by reaction of the corresponding metal hydroxide, the corresponding alcohol and calcium oxide in the presence of a suitable surfactant. The suitable surfactants are certain classes of cationics, non-ionics and amphoterics with cationic groupings. The surfactant causes the reaction to proceed much more rapidly and the formed alkoxide remains in solution with calcium hydroxide being formed as a precipitate which can be easily separated from the solution.

9 Claims, No Drawings

PRODUCTION OF SODIUM AND POTASSIUM ALKOXIDES

CROSS REFERENCE TO RELATED APPLICATION

This application is a continuation-in-part of my copending application Ser. No. 4,712, filed Jan. 19, 1979, entitled "Production of Sodium and Potassium Alkoxides now abandoned".

BACKGROUND OF THE INVENTION

Sodium and potassium alkoxides have been known for about 100 years and have been used commercially for various purposes for more than 50 years. However, no truly satisfactory way of manufacturing these substances cheaply, efficiently and with low energy costs have been found.

One of the oldest and simplest methods known in the art for the manufacture of these alkoxides is the reaction of an anhydrous alcohol with the respective metal, sodium or potassium. This reaction, however, involves the danger and inconvenience of using a highly reactive metal and the need for subsequent handling of the evolved hydrogen gas.

U.S. Pat. No. 1,712,830 suggests the reaction of sodium hydroxide with an anhydrous alcohol of at least 2 carbon atoms with azeotropic removal of the formed water by means of an inert solvent. Not only is azeotropic removal of water difficult, expensive and time consuming, but it cannot be done when the alcohol is methyl alcohol.

U.S. Pat. No. 2,278,550 involves the reaction of an alkali metal salt of a weak acid with an alcohol, e.g. anhydrous sodium sulfide and methanol to form sodium methoxide and sodium hydrogen sulfide. As is apparent, the subsequent handling of the toxic and foul smelling hydrogen sulfide presents considerable problems.

U.S. Pat. Nos. 2,796,443 and 2,877,274 involve the reaction of sodium hydroxide with alcohols using various column and distillation techniques. However, the engineering is difficult and complex and there is poor control over the process.

U.S. Pat. No. 2,437,272 describes the use of alkali metal amalgams in continuous flow processes. However the problem of this process is similar to the uses of alkali metals alone plus the additional problem of the toxic properties of the mercury contained in the amalgams.

U.S. Pat. No. 3,094,546 relates to the use of calcium carbide. However the byproduct is acetylene which of course requires special handling. In addition, calcium carbide is expensive and requires considerable energy in its production.

Bulgatsch, et al. in Chemisches Zentralblatt, Volume I (1939) page 642 describes the reaction of sodium hydroxide with calcium oxide at a temperature of 100°–130° C. and at a pressure of 4–5 atmospheres. Reaction at such high pressures and temperatures is difficult and expensive.

SUMMARY OF THE INVENTION

In accordance with the present invention a reaction is provided wherein sodium hydroxide or potassium hydroxide is reacted with an alcohol of up to six carbon atoms and unhydrated lime, i.e., calcium oxide, in the presence of a suitable surfactant, at atmospheric pressure. The reaction results in excellent yields of the corresponding sodium or potassium alkoxide in solution with the formed calcium hydroxide precipitating from the solution. The reaction proceeds much more rapidly with the surfactant present, than without any surfactant and satisfactory yields are obtained with the reaction carried out at relatively low temperatures, e.g., temperatures of up to about 60° C., and even at room temperature.

It is accordingly a primary object of the present invention to provide a simple and direct method of producing sodium and potassium alkoxides in high yield.

It is yet another object of the present invention to provide a method for the production of sodium and potassium alkoxides utilizing inexpensive reactants and involving low energy costs.

It is another object of the invention to provide for the production of sodium and potassium alkoxides by a method which is applicable not only to higher alcohols but even to methyl alcohol.

Other objects and advantages will be apparent from a further reading of the specification and of the appended claims.

With the above and other objects in view, the present invention mainly comprises the reaction of a reaction mixture consisting essentially of sodium or potassium hydroxide, an anhydrous alcohol and calcium oxide in the presence of a surfactant to form calcium hydroxide which precipitates and the corresponding metal alkoxide which remains in solution.

The precipitated calcium hydroxide in the alcoholic solution can be conveniently filtered off or separated by settling and decantation.

The precipitate is actually a mixture of calcium hydroxide, calcium methoxide and calcium hemimethoxide of variable composition.

The following are the classes of suitable surfactants or surface active agents:

Cationic surface active agents which are amine oxides and oxygen-containing amines (except those having amide linkages) as listed on page 297 of "Synthetic Organic Chemicals" published by the United States International Trade Commission, United States Production and Sales, 1977, USITC PUBLICATION 920, pages 286ff, the above grouping being listed at page 297. The following are surface active agents falling within the above group:

N, N-Bis(2-hydroxyethyl) (coconut oil alkyl)amine
N, N-Bis(2-hydroxyethyl)octadecylamine
N, N-Bis(2-hydroexthyl) (tallow alkyl)amine
(Coconut oil alkyl)amine, ethoxylated
(Coconut oil alkyl)amine, ethoxylated, acetate
(Coconut oil alkyl)amine, ethoxylated, oleate
N,N-Dimethylhexadecylamine oxide
Ethylenediamine, propoxylated
(Hydrogenated tallow alkyl)amine, ethoxylated
N-(2-hydroxyethyl)-N,N',N'-tris(2-hydroxyypropyl)-ethylenediamine
(Mixed alkyl)amine, ethoxylated
(9-Octadecenyl)amine, ethoxylated
Octadecylamine, ethoxylated
(Soybean oil alkyl)amine, ethoxylated
(Tallow aklyl)trimethylenediamine, ethoxylated
N-(Tallow alkyl)trimethylenediamine, ethoxylated
N,N,N',N'-Tetrakis(2-hydroxyethyl)ethylenediamine
N,N,N',N'-Tetrakis(2-hydroxypropyl)ethylenediamine, propoxylated and ethyoxylated
Triethanolamine, ethoxylated Amine oxides and oxygen-containing amines (Except those with amide linkages), acyclic, all other From the same book, other cationic surface agents are diamines and polyamines such as N-(coconut oil alkyl)trimethylenediamine listed at page 299, primary amines such as (coconut-oil alkyl)amine listed at page 299, amines not containing oxygen (and salts thereof) e.g., secondary and tertiary amines listed at page 300, oxygen-containing quaternary ammonium salts listed at pages 300 and 301, quaternary ammonium salts, not containing oxygen listed at pages 301 and 302.

The suitable nonionic surface active agents are glycerol esters of mixed acids listed at page 307, ethers listed at pages 308, 309 and 310.

The suitable amphoteric surface active agents are those which contain cationic groupings, namely:
(1-Carboxyheptadecyl)trimethylammonium hydroxide, inner salt
N-Dodecyl-$\beta$-alanine, partial sodium salt
N-dodecyl-3-iminodipropionic acid, disodium salt
N-(Dodecyl and tetradecyl)-$\beta$-alamine
N-(Tallow alkyl)-3-iminodipropionic acid, disodium salt In accordance with a further embodiment of the present invention it has been found desirable to leave a small amount of the solid, including unreacted calcium oxide, in the metal alkoxide solution where it acts as a protective agent against traces of atmospheric moisture or carbon dioxide which might inadvertently enter the stored alkoxide solution. The excess calcium oxide is thus found to be an excellent protective agent for the metal alkoxide solution.

The method of the present invention provides numerous advantages. In the first place, the reaction can be carried out under atmospheric pressure at room temperature as well as at elevated temperatures and the reaction can be carried out in steel equipment with only mild agitation. Furthermore, the produced byproduct, namely hydrated lime (calcium hydroxide) has a value which is substantially equal to that of the unhydrated starting material so that the economics of the process approach the simplest possible synthesis which would be the reaction of sodium hydroxide with the alcohol itself.

It should furthermore be noted that the particle size of the unhydrated lime is comparatively unimportant in the process and it is possible to use, with equal success, either powdered or lump material. The only difference of course is the time required for the reaction since lump would require a longer reaction time to produce the same effects at in the case of the powdered starting material. Still further it should be noted that even impure calcium oxide can be used provided that proper adjustment is made with respect to the quantities used and furthermore provided that not too much silica is present. The process has been successfully carried out using as poor a quality as 70% calcium oxide.

The overall reaction can be represented by the following equation:

$$MOH + CaO + R-OH \rightarrow R-OH + Ca(OH)_2$$

wherein M represents either sodium or potassium and R represent the alcohol substituent. In accordance with the preferred embodiment of the invention the carbon chain length of R should be six or less, although the process has been effectively carried out for the production of alkoxides of alcohols containing up to 22 carbon atoms.

In addition, the process of the present invention is equally applicable to reactions with glycols or other poly hydroxy alcohols, amino alcohols and other compounds which contain the alcoholic hydroxyl group, although obviously it is impractical to carry out the process where other groups are present which react with strong bases. For example, the method is inapplicable in the case of a starting material such as ethylene chlorohydrin.

DESCRIPTION OF PREFERRED EMBODIMENTS

The following examples are given to further illustrate the present invention and the advantages of using a surfactant in accordance therewith. The scope of the invention is not, however, meant to be limited to the specific details of the examples.

In all of the following examples, all parts are by weight.

EXAMPLE IA 150 parts of calcium oxide pebbles (about ½ inch in size), 40 parts caustic soda flakes, and 262 parts methanol were combined in a reaction vessel fitted with a reflux condenser and stirred with moderate speed at room temperature for 197 hours. The solid material in the reactor was allowed to settle and the supernatant liquid was carefully decanted away from the settled solids. The solution contained 11.76% $NaOCH_3$, 5.33% $NaOH$, and 0.09% $Na_2CO_3$, which constitutes a 61.8% yield of $NaOCH_3$.

EXAMPLE IB

Example IA is repeated however with the addition of 1% cetyl trimethyl ammonium chloride (with respect to the weight of the NaOH). After a reaction time of only 24 hours, the resulting solution contained 13.5% $NaOCH_3$.

EXAMPLE IC

Example IA was repeated however utilizing 1% Triton X100 (octyl phenol condensed with 9–10 mols ethyleneoxide). After only 24 hours the solution contained 10.7% $NaOCH_3$.

EXAMPLE ID

Example IA is repeated however with 1% sodium lauryl sulfate. After 144 hours the solution contained 11.6% $NaOCH_3$.

EXAMPLE IIA 99 parts methanol, 20 parts caustic soda flakes, and 75 parts calcium oxide, powdered, were combined in an apparatus similar to that in Example I and maintained between 45° C. and 60° C. for 54 hours with mild agitation. The decanted products was found to contain: 13.04% $NaOCH_3$, 8.36% $NaOH$, and 0.30% $Na_2CO_3$ which constitutes a 53.0% yield of $NaOCH_3$.

EXAMPLE IIB

Example IIA is repeated however with 2% cetyl pyridinium chloride. After 54 hours the solution contained 22.3% $NaOCH_3$.

EXAMPLE IIIA 14 parts of commercial 90% KOH flake. 71 parts methanol, and 38 parts calcium oxide were combined in an apparatus and procedure similar to Example I and stirred at room temperature for 190 hours. The product was found to contain 14.7% $KOCH_3$, 3.49% KOH, and 0.38% $K_2CO_3$ which constitutes a 75.7% yield of $KOCH_3$.

EXAMPLE IIIB

Example IIIA is repeated with 1% cetyl pyridinium chloride. After only 24 hours the solution contained 17.1% $KOCH_3$.

EXAMPLE IIIC

Example IIIA is repeated however with 1.5% Triton N101 (nonylphenol condensed with 9-10 mols ethyleneoxide). After only 24 hours the solution contained 16.2% $KOCH_3$.

EXAMPLE IIID

Example IIIA is repeated with 2% cetyl trimethyl ammoniumbromide. After 24 hours the solution contained 21.4% $KOCH_3$.

EXAMPLE IVA 18 parts commercial caustic soda flakes, 76 parts calcium oxide and 242 parts ethanol were combined in an apparatus similar to Example I and stirred at room temperature for 24 hours. The product was found to contain 3.05% $NaOC_2H_5$, 5.42% NaOH, 0.44% $Na_2CO_3$ which shows a 23.8% conversion to sodium ethylate.

EXAMPLE IVB

Example IVA is repeated with ½% Triton X102 (octyl phenol condensed with 12-13 mols ethyleneoxide). After 24 hours the solution contained 12.2% $NaOC_2H_5$.

Similar results are obtained in the reaction of tertiary butanol with caustic potash flakes and calcium oxide to produce $KOC(CH_3)_3$.

The amount of the surfactant is not critical. Very small amounts can be used. While relative large amounts can also be used, it is of course desirable to use as little as possible of the surfactant from the standpoint of economy. In general, amounts of 0.1-4.0% of surfactant, with respect to the amount of the sodium or potassium hydroxide, can be used. The amount is preferably between about 0.5 and 2% by weight.

While the invention has been illustrated in particular with respect to specific reactants for the production of specific alkoxides, it is apparent that variations and modifications can be made.

What is claimed is:

1. Method of producing sodium and potassium alkoxides, which comprises reacting a reaction mixture consisting essentially of calcium oxide, an alcohol of up to 6 carbon atoms, and an anhydrous metal hydroxide wherein the metal is sodium or potassium in the presence of a surfactant to form the corresponding metal alkoxide and calcium hydroxide, said surfactant being present in an amount of 0.1-4% of the anhydrous metal oxide and being selected from the group consisting of cationic amine oxides and oxygen containing amines other than those having amide linkages, cationic diamines and polyamines, cationic primary monoamines, cationic secondary and tertiary monoamines, cationic oxygen-containing quaternary ammonium salts, cationic quarternary ammonium salts not containing oxygen, nonionic glycerol esters of mixed acids, nonionic ethers and amphoteric surfactants selected from the group consisting of (1-carboxyheptadecyl) trimethylammonium hydroxide, inner salt, N-dodecyl-8-alanine, partial sodium salt, N-dodecyl-3-iminodipropionic acid, disodium salt, N-(dodecyl)-8-alamine, N-(tetradecyl)-8-alanine, and N-(tallow alkyl)-3-iminodipropionic acid, disodium salt.

2. Method according to claim 1 wherein said surfactant is a nonionic glycerol ester of mixed acids, or a surface active ether.

3. Method according to claim 1 wherein said surfactant is an amphoteric surfactant selected from the group consisting of
   (1-(carboxyheptadecyl)trimethylammonium hydroxide, inner salt,
   N-dodecyl-8-alanine, partial sodium salt,
   N-dodecyl-3-iminodipropionic acid, disodium salt,
   N-(dodecyl)-8-alanine,
   N-(tetradecyl)-8-alanine, and
   N-(tallow alkyl)-3-iminodipropionic acid, disodium salt.

4. Method according to claim 1 wherein said surfactant is a cationic amineoxide, cationic oxygen containing amine other than those having amide linkages, cationic diamine, cationic polyamine, cationic primary monoamine, cationic secondary monoamine, cationic tertiary monoamine, cationic oxygen containing quaternary ammonium salt or a cationic quaternary ammonium salt not containing oxygen.

5. Method according to claim 1 wherein the reaction is effected under atmospheric pressure.

6. Method according to claim 5 wherein the reaction is effected at a temperature of up to 60° C.

7. Method according to claim 1 wherein the formed calcium hydroxide which remains undissolved is separated from the metal alkoxide which is in solution.

8. Method according to claim 1 wherein an excess of calcium oxide is used.

9. Method according to claim 1 wherein an excess of calcium oxide is used and wherein some calcium oxide is permitted to remain in the metal alkoxide reaction solution where it acts to protect the metal alkoxide from atmospheric deterioration.

* * * * *